United States Patent [19]

Denton

[11] Patent Number: 5,487,731
[45] Date of Patent: Jan. 30, 1996

[54] ESOPHAGEAL INTUBATION DETECTOR WITH INDICATOR

[75] Inventor: Marshall T. Denton, Salt Lake City, Utah

[73] Assignee: Wolfe Tory Medical, Inc., Salt Lake City, Utah

[21] Appl. No.: 199,628

[22] Filed: Feb. 22, 1994

[51] Int. Cl.$^6$ .................................................. A61M 29/00
[52] U.S. Cl. ............... 604/100; 128/202.22; 128/207.15
[58] Field of Search ..................... 604/100; 128/200.24, 128/200.26, 202.22, 205.23, 207.14, 207.15

[56] References Cited

U.S. PATENT DOCUMENTS

| | | | |
|---|---|---|---|
| 2,638,096 | 5/1953 | Waldhaus | 128/348 |
| 4,879,999 | 11/1989 | Leiman et al. | |
| 5,056,514 | 10/1991 | DuPont | 128/207.14 |
| 5,135,488 | 8/1992 | Foote et al. | 604/97 |
| 5,163,904 | 11/1992 | Lampropoulos et al. | 604/100 |

OTHER PUBLICATIONS

The capnographer discussed on p. 2 and 3 of the specification.
The Easy Cap End-Tidal $CO_2$ detector discussed on p. 3 of the specification.
Two page instructions for the "Esophageal Intubation Detector (EID)" prepared by Wolfe Tory Medical, Inc. in 1993.
510(k) Notification from Wolfe-Carney Medical for market clearance from the Food and Drug Administration, dated Feb. 8, 1993, 32 pages.
B. A. MacLeod et al., "Verification of Endotracheal Tube Placement with Colorimetric End-Tidal $CO_2$ Detection," Annals of Emergency Medicine, 20:3 Mar. 1991, pp. 267–270 (78–81).
M. Y. K. Wee, "The Oespohageal Detector Device: Assessment of a New Method to Distinguish Oesophageal from Tracheal Intubation," Anaesthesia, 1988, 43:27–29.
K. N. Williams et al., "The Oesophageal Detector Device: A Prospective Trial of 100 Patients," Anaesthesia, 1989, 44:412–14.
S. T. Sum Ping et al., "Accuracy of the FEF $CO_2$ Detector in the Assessment of Endotracheal Tube Placement," Anesth Analg, 1992, 74:415–19.
W. R. Anton, "A Disposable End-Tidal $CO_2$ Detector to Verify Endotracheal Intubation," Annals of Emergency Medicine, 20:3 Mar. 1991, pp. 271–275 (82–86).
R. G. Foutch et al., "The Esophageal Detector Device: A Rapid and Accurate Method for Assessing Versus Esophageal Intubation in a Porcine Model", Annals of Emergency Medicine, Sep. 1992, 21:9, pp. 1073–1076 (43–46).
J. J. O'Leary, "A Method of Detecting Oesophageal Intubation or Confirming Tracheal Intubation," Anaesth Intens Care (1988), 16, pp. 299–301.

(List continued on next page.)

*Primary Examiner*—Corrine M. McDermott
*Attorney, Agent, or Firm*—Trask, Britt & Rossa

[57] ABSTRACT

An esophageal intubation detector with an indicator is used to determine whether the hollow tip of an endotracheal tube is in the esophagus or trachea of a patient. In a preferred embodiment, the esophageal intubation detector includes a syringe which is connected to the endotracheal tube through an adapter to which the indicator is connected. In practice, a clinician places the endotracheal tube into, for example, a patient's mouth and throat. The esophageal intubation detector is connected to the endotracheal tube creating a system. The system volume increases through retraction of a syringe plunger or self-inflation of a depressed bulb. If the tube tip is in the esophagus, the tube tip will become occluded with the walls of the esophagus as the system volume increases, causing the system pressure to decrease. A decrease in system pressure causes activation of the indicator, implying that the endotracheal tube is in the esophagus. By contrast, if the tube tip is in the trachea, the tube tip remains open as the system volume increases and free aspiration of air occurs. The system pressure remains relatively constant and the indicator is not activated, implying the endotracheal tube is in the trachea. Activation of the indicator may result in audible or visual (or both) signs to inform the clinician of the position of the tube tip.

22 Claims, 8 Drawing Sheets

OTHER PUBLICATIONS

W. A. Jenkins et al., "The Syringe Aspiration Technique to Verify Endotracheal Tube Position," from NAEMSP Abstracts, presented Jun. 19, 1992, Abstract in Prehospital and Disaster Medicine, 1992, vol. 7, Suppl. 1, 12S.

D. Oberly et al., "An Evaluation of the Esophageal Detector Device Using a Cadaver Model," Amer. J. of Emergency Medicine, vol. 10, No. 4, Jul. 1992, pp. 317–320.

P. L. Donahue, "The Oesophageal Detector Device", Anaesthesia, 1994, vol. 49, pp. 863–865.

W. A. Jenkins et al., "The Syringe Aspiration Technique to Verify Endotracheal Tube Position" American Journal of Emergency Medicine, Jul. 1994, vol. 12, No. 4, pp. 413–415.

W. P. Bozeman et al., "The Esophageal Detector Device Versus End Tidal $CO_2$ Detection in Emergency Intubations," from SAEM 1994 Annual Meeting Abstracts, 1994, 1(2) A77, #232 (Abstract in Academic Emerg Med).

K. H. Andersen et al., Forum "Assessing the position of the tracheal tube. The reliability of different methods." Anaesthesia, 1989, vol. 44, pp. 984–985.

Linda Zaleski et al., "The Esophageal Detector Device, Does it Work?", Anesthesiology, 1993, 79:244–47.

M. R. Salem et al., "Use of the Self–Inflating Bulb for Detecting Esophageal Intubation After Esophageal Ventilation," Anesth Analg, 1993, 77:1227–31.

M. R. Salem et al., "Efficacy of the Self–inflating Bulb in Detecting Esophageal Intubation, Does the Presence of a Nasogastric Tube or Cuff Deflation Make a Difference?", Anesthesiology, Jan. 1994, 80:42–48.

N. S. Morton et al., "The Oesophageal Detector Device: Successful Use in Children," Correspondence, Anaesthesia, 1989, 44:523–24.

A. Baraka et al., "The Esophageal Detector Device in the Morbidly Obese," Letters to the Editor, Anesth Analg, 1993, 77(2):400.

M. K. Y. Wee, "Comments on the Oesophageal Detector Device," Correspondence, Anaesthesia, 1989, 44:930–31.

A. Baraka, "The Oesophageal Detector device in the asthmatic patient," Correspondence, Anaesthesia, 1993, 48(3):275.

S. R. Haynes et al., "Use of the oesophageal detector device in children under one year of age," Anaesthesia, 1990, vol. 45, pp. 1067–1069.

N. S. Morton et al., "The Oesophageal Detector Device: Successful Use in Children," from Royal Hospital for Sick Children, Glasgow G3 8SJ.

A. Baraka et al., "The Esophageal Detector Device in the Morbidly Obese," Anesth Analg, 1993, 77:398–410.

"Comments on the Oesophageal Detector Device" from Correspondence p. 930.

A. Baraka, "Oesophageal Detector device in the asthmatic patient." (single page).

S. R. Haynes et al., "Use of the oesophageal detector device in children under one year of age," Anaesthesia, 1990, vol. 45, pp. 1067–1069.

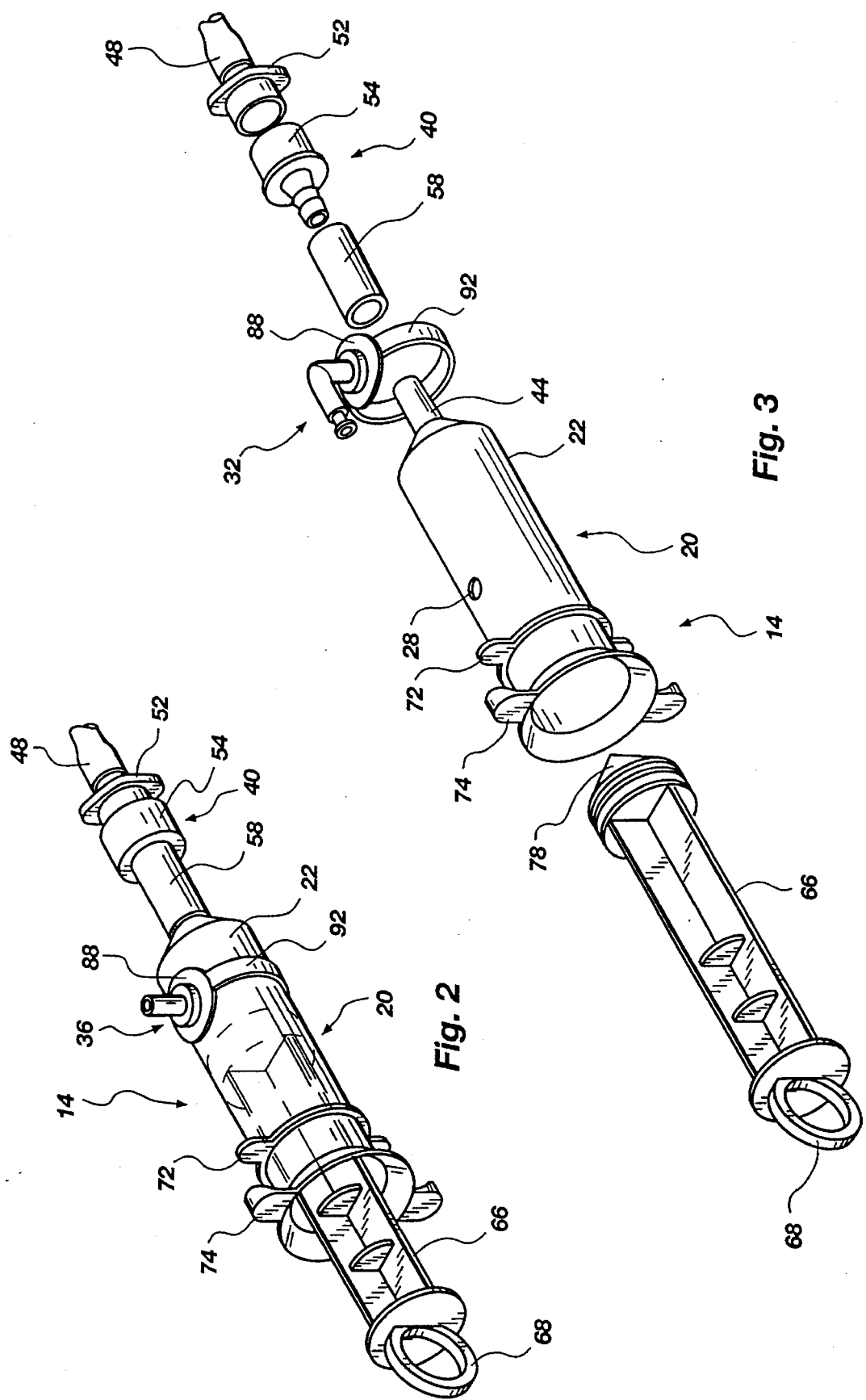

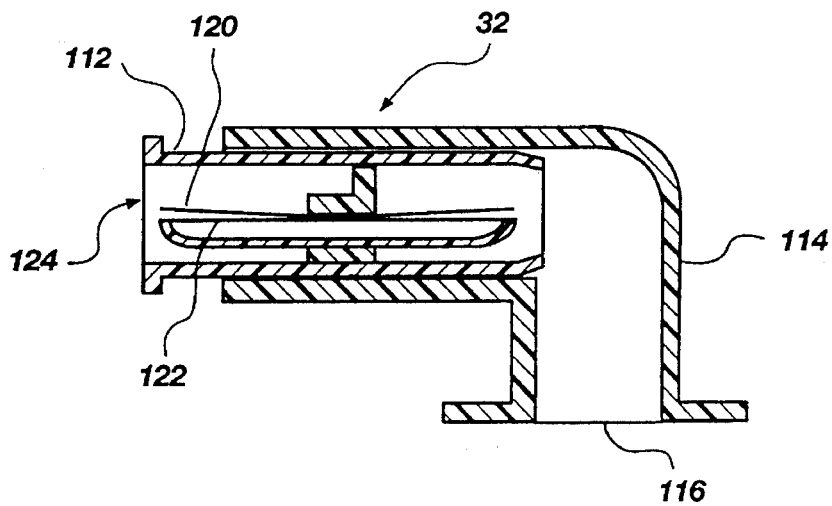
Fig. 4
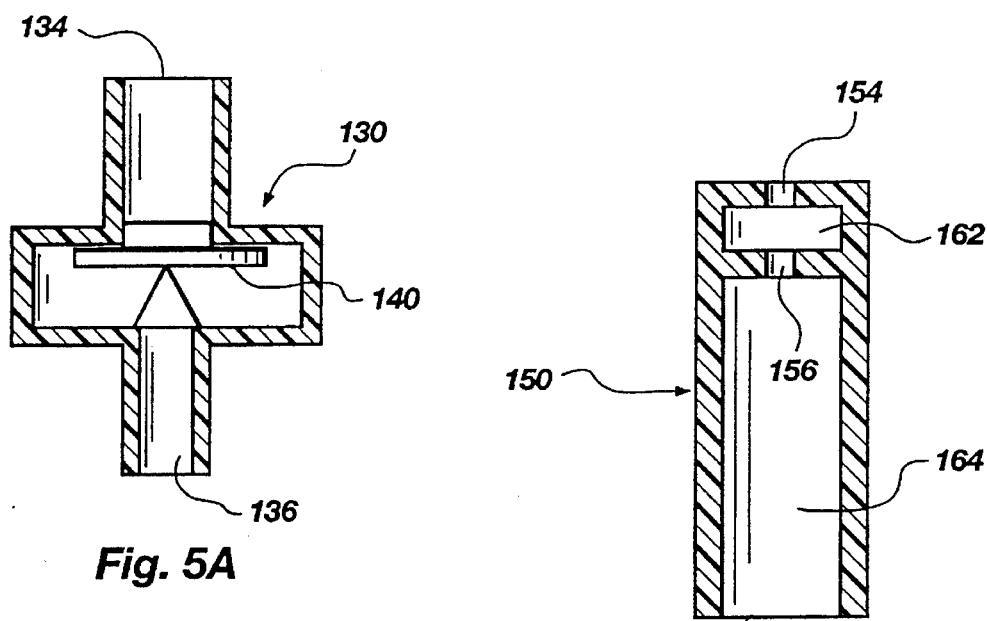
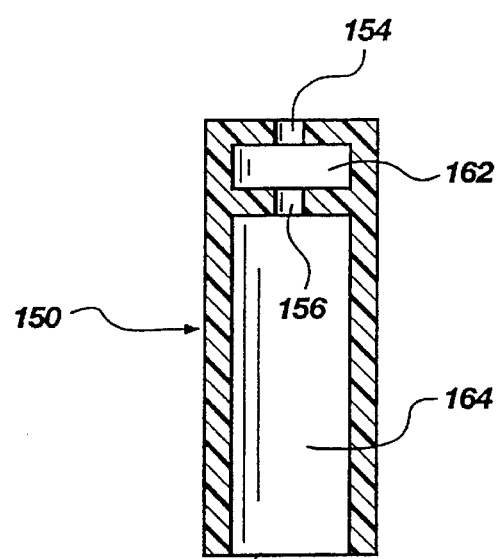
Fig. 6A
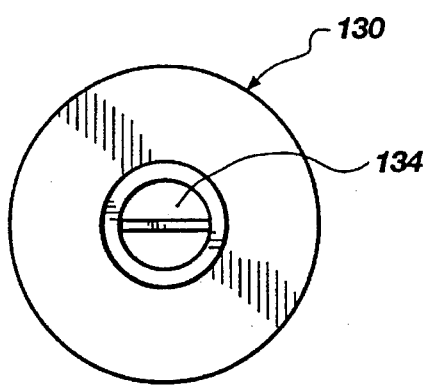
Fig. 5A
Fig. 5B
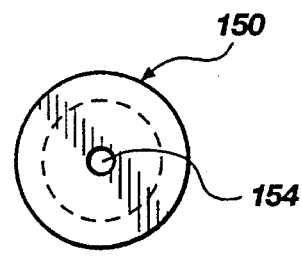
Fig. 6B

ESOPHAGEAL INTUBATION DETECTOR WITH INDICATOR

BACKGROUND OF THE INVENTION

1. Field of the Invention

The present invention relates to an esophageal intubation detector and, more particularly, to an esophageal intubation detector with an indicator that indicates whether an endotracheal tube is in a patient's esophagus or in the patient's trachea, immediately following an attempted intubation.

2. State of the Art

Endotracheal tubes may be used to pump oxygen enriched air into the lungs of a patient. The procedure is used in the operating room, the emergency department, and pre-hospital care settings, such as accident sites. One end of the endotracheal tube is connected to a source of oxygen and the other end is placed in the patient's trachea, in a procedure referred to as intubation. A danger in intubation is that the endotracheal tube may be placed in the esophagus rather than the trachea. Even an experienced clinician may have difficulty in properly placing the endotracheal tube. Improper placement of the tube may result in permanent injury or death. Accordingly, detection of improper placement of the endotracheal tube is extremely important.

Clinical examination alone is dependent on the clinician's experience and judgement and may give misleading results. For this reason, accessory devices exist that help determine if the trachea is properly intubated. For example, capnographers have been used to detect improper placement. A capnographer is an expensive instrument that detects the presence of $CO_2$. Confirmation of proper endotracheal tube placement is based on the fact that carbon dioxide is present in exhaled air in approximately 5% concentration, but is present in esophageal gas in only minute concentrations. The capnographer is a relatively large, sophisticated, and expensive reusable instrument that has a valid use in hospital operating rooms. The capnographer is too bulky, too expensive, and requires too much time to calibrate for routine use in prehospital settings and emergency departments. Unfortunately, it is these settings where experience may be limited and where esophageal intubations more frequently occur.

The EASY CAP End-Tidal $CO_2$ detector is a currently available disposable device for use outside the operating room that assists in distinguishing esophageal from tracheal intubations by a color indication. The EASY CAP End-Tidal CO2 detector is marketed by Nellcor Inc. (formerly produced and distributed by FENEM Airway Management Systems under the name "FEF End-Tidal $CO_2$ detector"). After intubation is performed, the End-Tidal $CO_2$ Detector is attached to the endotracheal tube in line with the oxygen bag. Oxygen is insufflated through the device into the endotracheal tube and lungs, then exhaled back through the device. A change of color from purple to yellow with each breath indicates tracheal intubation. If the endotracheal tube is in the esophagus, no $CO_2$ is detected and the color change does not occur.

The $CO_2$ Detector device will not easily detect tracheal intubation in the patient who is pulseless or inadequately perfusing the pulmonary circulation. This is due to inadequate $CO_2$ exhalation. It will still detect esophageal intubation in these patients. However, many tracheal intubations will be interpreted as esophageal due to lack of color change. Clinical judgement is required in these cases.

Another technique for distinguishing esophageal from tracheal intubation is described in M. Y. K. Wee, "The oesophageal detector device assessment of a new method to distinguish oesophageal from tracheal intubation," *Anaesthesia*, 43:27–29 (1988). This technique relies on the relative rigidity of the tracheal wall, as compared to that of the esophagus. The trachea remains constantly patent due to C-shaped rings of cartilage supporting its lumen. The esophagus will collapse over the end of a rigid tube when significant negative pressure (with respect to atmospheric pressure) is applied in the tube, thus preventing aspiration of air. The more rigid trachea, on the other hand, remains open and allows free aspiration of air, when significant negative pressure is applied in the tube.

Under the technique, a detector device includes a syringe that is attached to an adaptor. After intubation, the adaptor is connected to the endotracheal tube. Air is aspirated into the syringe by pulling the syringe plunger. Free flow of air (i.e., ease in pulling the syringe plunger) is indicative of proper tube placement in the trachea. Resistance to flow (i.e., resistance to pulling the syringe plunger) is indicative of that the endotracheal tube may be improperly placed.

SUMMARY OF THE INVENTION

In one embodiment of the invention, an esophageal intubation detector includes a syringe having an orifice in the syringe barrel. An indicator, which is positioned over the orifice, indicates whether an endotracheal tube is in a patient's esophagus or in the patient's trachea. A variety of indicators, including audible, visual, and transducer indicators, may be used. The indicators provide an audible, visual, and/or electrical signal indicating the position of the endotracheal tube. Some indicators may only provide signals indicating the endotracheal tube is in the esophagus. The clinician infers that the endotracheal tube is in the trachea from the absence of the signal. Other indicators may provide signal(s) that positively indicate that the endotracheal tube is in the trachea, or the signal(s) from the indicator may be processed to positively indicate that the endotracheal tube is in the trachea.

In operation, a clinician inserts an endotracheal tube into the throat of a patient. The tip of the endotracheal tube includes holes. With the syringe plunger pushed toward the tip of the syringe, the clinician connects the syringe to the endotracheal tube. The clinician then pulls the plunger away from the syringe tip causing the system volume in the esophageal intubation detector and endotracheal tube to increase. If the tip of the endotracheal tube is in the esophagus, the holes in the tip will become occluded with the walls of the esophagus as the plunger is pulled causing the system pressure to decrease. The system pressure decreases until the plunger seal reaches the orifice. The present invention includes both vented and non-vented indicators. In the case of a vented indicator, the system pressure suddenly increases when the plunger seal passes the orifice. The indicator may be activated by detection of a change in the pressure or by flow of air created by the pressure differential. In the case of a non-vented indicator, the system pressure remains negative when the plunger seal passes the orifice, however, the pressure detected by the indicator will suddenly change, activating the indicator. If the tip of the endotracheal tube is in the trachea, the holes in the tip remain open and the pressure in the syringe remains relatively constant. Consequently, the indicator is not activated.

The present invention is not limited to using a syringe, but may include other sources of negative pressure. The indicator may provide signals to a remote audio and/or visual communication device.

BRIEF DESCRIPTION OF THE DRAWINGS

FIG. 2 is a perspective view of an esophageal intubation detector including a second embodiment of an audible indicator and connected to an endotracheal tube.

FIG. 3 is an exploded view of the esophageal intubation detector of FIG. 1 and a portion of the endotracheal tube.

FIG. 4 is a side sectional view of the first embodiment of an audible indicator.

FIG. 5A is a side sectional view of a third embodiment of audible indicator.

FIG. 5B is a top view of the third embodiment of audible indicator shown in FIG. 5A.

FIG. 6A is a side sectional view of a fourth embodiment of audible indicator.

FIG. 6B is a top view of the fourth embodiment of audible indicator shown in FIG. 6A.

DETAILED DESCRIPTION OF PREFERRED EMBODIMENTS

Figure 1:
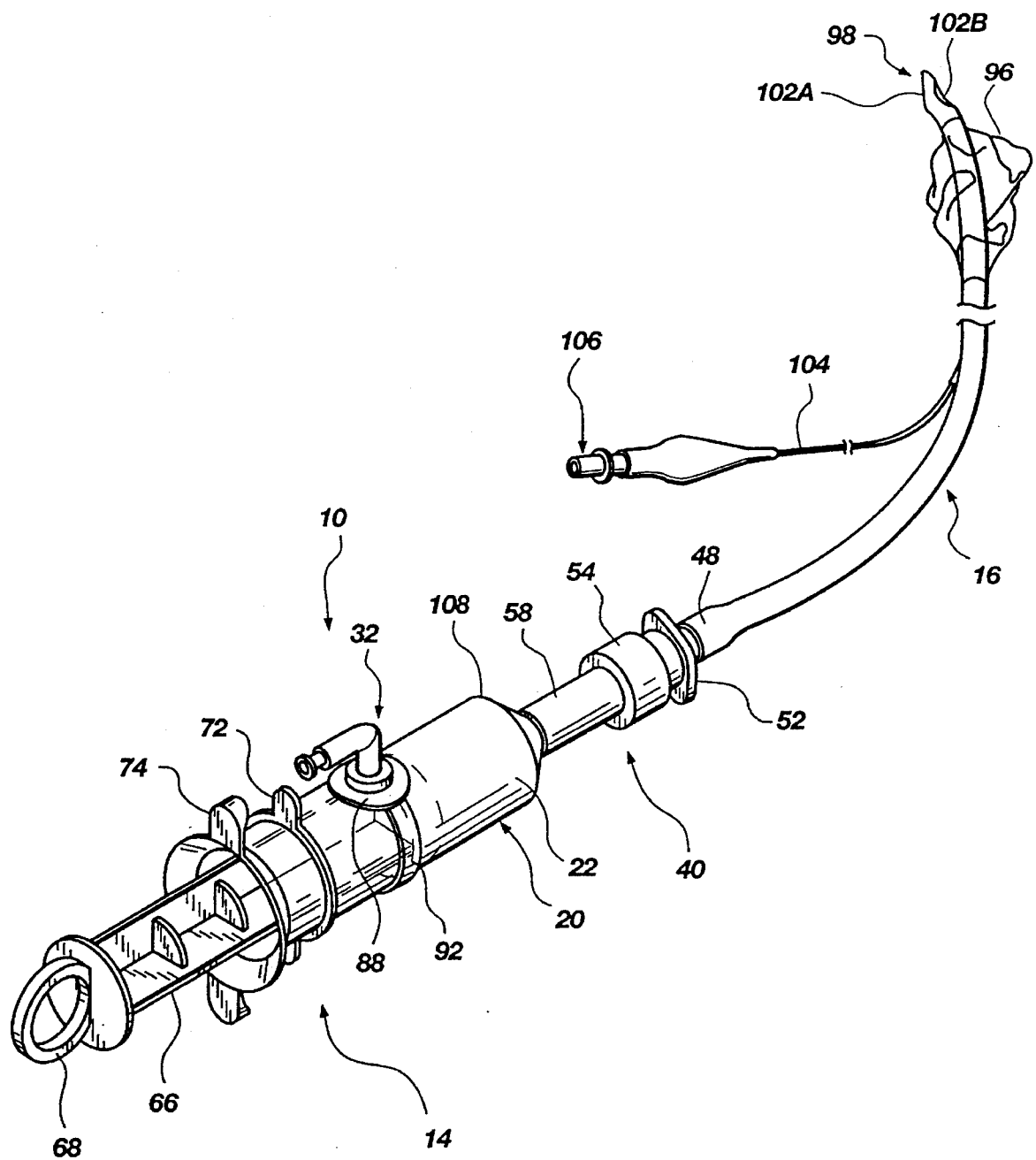
FIG. 1 is a perspective view of an esophageal intubation detector including a first embodiment of an audible indicator and connected to an endotracheal tube.

Referring to FIGS. 1, 2, and 3, an esophageal intubation detection system 10 includes an esophageal intubation detector 14 and an endotracheal tube 16. In a first embodiment, esophageal intubation detector 14 includes a syringe such as standard catheter tip syringe 20 having a barrel 22. As shown in FIG. 3, barrel 22 includes an orifice 28 over which an indicator is secured in place.

As described herein, a variety of indicators may be used. In FIGS. 1 and 3, the indicator is an audible indicator 32, which is a first embodiment of an audible indicator. In FIG. 2, the indicator is an audible indicator 36, which is a second embodiment of an audible indicator.

Referring to FIGS. 1-3, esophageal intubation detector 14 is connectable to endotracheal tube 16 by means of an adapter 40. It is contemplated that esophageal intubation detector 14 and endotracheal tube 16 may be sold separately or together, and if sold together, in a connected or disconnected condition.

The following components of esophageal intubation detector 14 are assembled before the time of intubation. Typically, assembly will occur by the manufacturer. Adapter 40 includes a female adapter 54 and a connection tube 58. One end of connection tube 58 is connected to a syringe tip 44 and the other end of connection tube 58 is connected to female adapter 54.

Syringe 20 includes a plunger 66 having a ring handle 68 and a plunger seal 78. Syringe 20 may include handles 72 and 74 for ease in moving plunger 66. Before intubation, plunger 66 is positioned so that plunger seal 78 is near syringe tip 44. The indicator, such as indicator 32, may be held in place by a base 88 that is secured to barrel 22 over orifice 28 with a strap 92. Base 88 and strap 92 are preferably made of rubber or flexible silicone which fits around barrel 22 and forms a hermetic seal with barrel 22. Base 88 and strap 92 may be formed or joined as a unit. Alternatively, base 88 may be glued to barrel 22.

Endotracheal tube 16 includes a tube 48 and an end adapter 52 at one end of tube 48. Endotracheal tube 16 includes an inflatable balloon 96 and a tip 98 with holes 102A and 102B. Balloon 96 may be inflated through a tube 104 and connection port 106.

At the time of intubation, a clinician inserts tip 98 of endotracheal tube 16 into the throat of the patient. After initial intubation, the clinician connects female adaptor 54 of adaptor 40 with end adaptor 52 of endotracheal tube 16. The clinician then pulls plunger 66 away from syringe tip 44.

As used herein, the volume in barrel 22 and tube 48 between plunger seal 78 and tip 98 of endotracheal tube 16 is referred to as the "system volume." The air pressure in barrel 22 and tube 48 between plunger seal 78 and tip 98 is referred to as the "system pressure." As plunger 66 is pulled away from syringe tip 44, the system volume increases. If either hole 102A or hole 102B is open, the system pressure remains relatively constant as plunger 66 is pulled away from syringe tip 44. If holes 102A and 102B are occluded, the system pressure substantially decreases as plunger 66 is pulled away from syringe tip 44. However, when plunger seal 78 moves past orifice 28, the system pressure rapidly increases as air rushes through indicator 32 and orifice 28. When endotracheal tube 16 is in the esophagus, the esophagus collapses over and occludes holes 102A and 102B when negative pressure is applied in tube 48. By contrast, when endotracheal tube 16 is in the trachea, the trachea remains rigid next to holes 102A and 102B allowing free aspiration of air, when negative pressure is applied in tube 48.

Indicators 32 and 36 produce a sound in response to air rapidly moving through the indicator. The noise indicates to the clinician that intubation may be improper.

FIG. 4 shows a cross-section of a side view of audible indicator 32, which includes a whistle 112 in a housing 114. Housing 114 includes an orifice 116 which is aligned with and sealed around orifice 28. Whistle 112 includes an orifice 124, and reed elements 120 and 122, which create a noise when air passes through them. When plunger seal 78 passes by orifice 28, air passes through orifice 124 toward orifices 116 and 28. Indicator 36 is very similar to indicator 32, except that indicator 36 is perpendicular rather than parallel to barrel 22.

A comparison of FIGS. 1 and 3 with FIG. 2 shows that orifice 28 (beneath audible indicator 36) is positioned closer to tip 44 in FIG. 2 than is orifice 28 in FIGS. 1 and 3. There are some tradeoffs in the choice of positioning orifice 28. The following are factors to consider. First, at least some significant negative pressure is required to properly activate an indicator (e.g., to be sufficiently loud to be heard). This would suggest moving the orifice 28 farther from syringe tip 44, as a significant negative pressure is required to close the esophagus around holes 102A and 102B. Second, the farther orifice 28 is from syringe tip 44, the more effort is required to pull plunger 66 and the greater the reduction in pressure and/or the longer the reduction in pressure. It is expected that in many cases, a preferable distance between audible indicator 32 and syringe tip 44 would be about the same as or even greater than that of the arrangement of FIG. 1.

FIGS. 5A and 5B shows side and top views of an audible indicator 130, which is a third embodiment of an audible indicator. Audible indicator 130 includes an orifice 134 and an orifice 136, which is aligned with and sealed around orifice 28. When plunger seal 78 passes by orifice 28, air passes through orifice 134 toward orifices 136 and 28 causing a disk 140 to vibrate and a sound to be produced thereby.

FIGS. 6A and 6B shows side and top views of an audible indicator 150, which is a fourth embodiment of an audible indicator. Audible indicator 150 includes small diameter orifices 154 and 156, and a larger diameter orifice 158, which is aligned with and sealed around orifice 28. Audible indicator 150 includes cavities 162 and 164. When plunger seal 78 passes by orifice 28, air passes through orifices 154 and 156 toward orifices 158 and 28 causing a sound to be produced.

Figure 7:
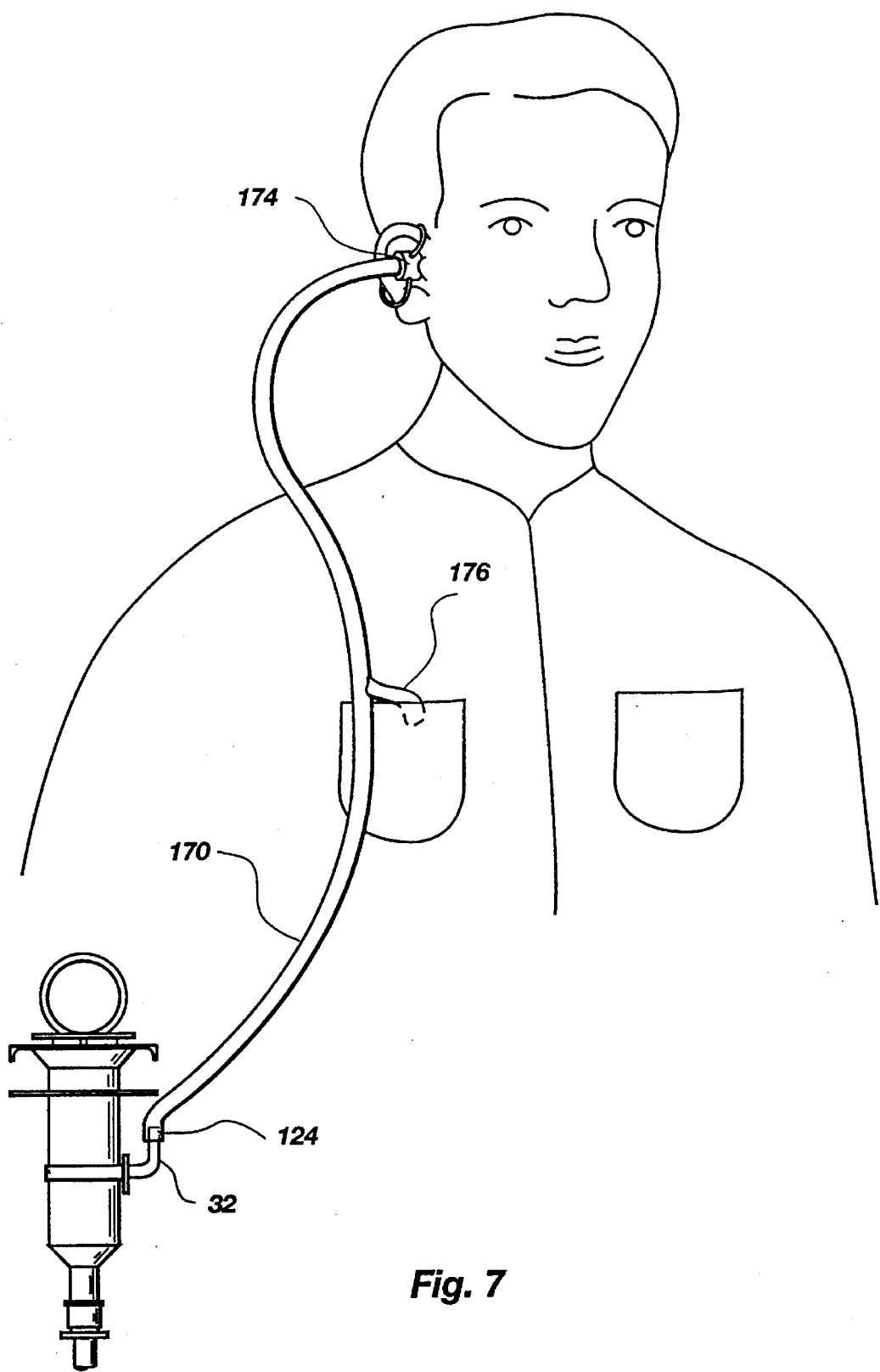
FIG. 7 is a perspective view of an extension tube that connects an audible indicator of an esophageal intubation detector to an ear piece fitting into the ear of a clinician.

Emergency settings in which esophageal intubation detection system 10 may be used are often noisy. Referring to FIG. 7, a tube 170 is connected between orifice 124 of audible indicator 32 and an ear piece 174 clipped to the ear of a clinician. A clip 176 may be clipped to the clothing of the clinician to prevent ear piece 174 from being pulled from the clinician's ear. Of course, tube 170 may be used in connection with the other audible indicators.

Figure 8A:
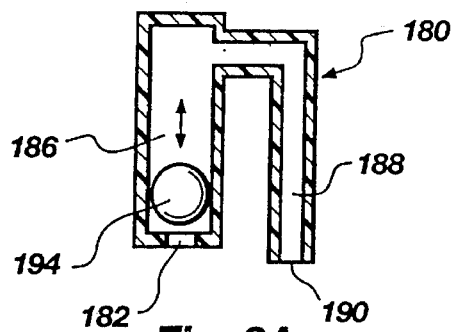
FIG. 8A is a side sectional view of a first embodiment of visual indicator.
Figure 8B:
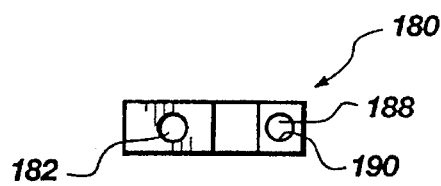
FIG. 8B is a top view of the first embodiment of visual indicator shown in FIG. 8A.

As an alternative or addition to an audible indicator, a visual indicator may be used to provide an indication of whether intubation is proper. FIGS. 8A and 8B show side and top views of a transparent visual indicator 180, which is a first embodiment of a visual indicator. Visual indicator 180 includes a cavity 186 between an orifice 182 and a tube 188. Tube 188 includes an orifice 190, which is aligned with and sealed around orifice 28. When significant negative pressure is created (because holes 102A and 102B are occluded) and plunger seal 78 passes by orifice 28, air passes through orifice 182 and towards orifices 190 and 28 causing a ball 194 to rise, indicating that endotracheal tube 16 is in the esophagus rather than the trachea. Ball 194 may be made of or covered with glow in the dark material for ease of sight during low light conditions.

Figure 9A:
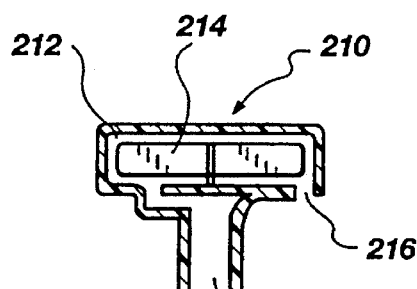
FIG. 9A is a side sectional view of a second embodiment of visual indicator.
Figure 9B:
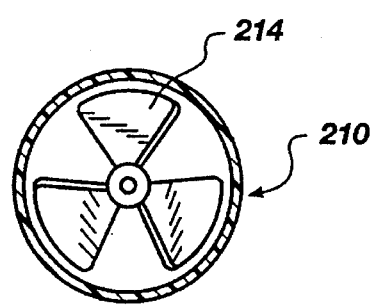
FIG. 9B is a top view of the second embodiment of visual indicator shown in FIG. 9A.

FIGS. 9A and 9B show side and top views of a visual indicator 210, which is a second embodiment of a visual indicator. Visual indicator 210 includes a cavity 212 in which a paddle wheel 214 is suspended, and orifices 216 and 218. Orifice 218 is aligned with and sealed around orifice 28. When plunger seal 78 passes by orifice 28, air passes through orifice 216 toward orifices 218 and 28 causing paddle wheel 214 to spin indicating that intubation may have been in the esophagus rather than the trachea. Wheel 214 may be made of glow in the dark material.

Indicators 32, 36, 130, 150, 180, and 210 are examples of vented indicators in that when plunger seal 78 passes orifice 28, the system pressure increases. The indicator illustrated in FIGS. 10A and 10B is an example of a non-vented indicator.

Figure 10A:
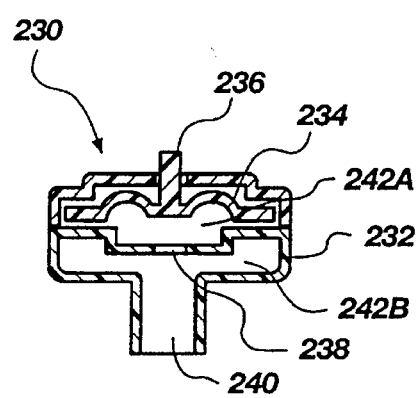
FIG. 10A is a side sectional view of a third embodiment of visual indicator.
Figure 10B:
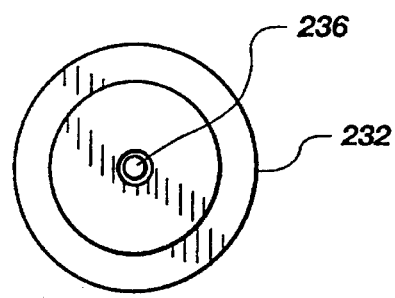
FIG. 10B is a top view of the third embodiment of visual indicator shown in FIG. 10A.

FIGS. 10A and 10B show side and top views of a visual indicator 230, which is a third embodiment of a visual indicator. Visual indicator 230 includes a housing 232 that encloses a silicone diaphragm 234. An orifice 238 separates cavities 242A and 242B within housing 232. Silicone diaphragm 234 is connected to an indicator post 236. Visual indicator 230 includes an orifice 240, which is aligned with and sealed around orifice 28 in syringe 20. When endotracheal tube 16 is in the esophagus, the system pressure decreases as plunger 66 is pulled away from syringe tip 44. When plunger seal 78 passes orifice 28, the pressure inside cavities 242A and 242B suddenly decreases causing silicone diaphragm 234 to pull indicator post 236 toward syringe barrel 22, indicating that endotracheal tube 16 may have been in the esophagus rather than the trachea. Indicator post 236 may be made of glow in the dark material. Alternatively, visual indicator 230 could be designed so that indicator post 236 pops up rather than down.

Figure 11:
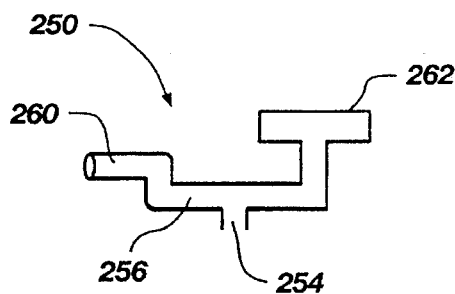
FIG. 11 shows a side view of a combined indicator including both audio and visual indicators.

FIG. 11 shows a combination audio and visual indicator 250. An orifice 254 in a T-connector tube 256 is aligned with and sealed around orifice 28 in syringe 20. T-connector tube 256 is connected to an audible indicator 260 (which may be any of the above-described audible indicators or an other audible indicator) and a visual indicator 262 (which may be any of the above-described visual indicators or an other visual indicator). Rather than using a connector tube, there could be two orifices, preferably at the same distance from syringe tip 44, connected to two indicators.

Figure 12:
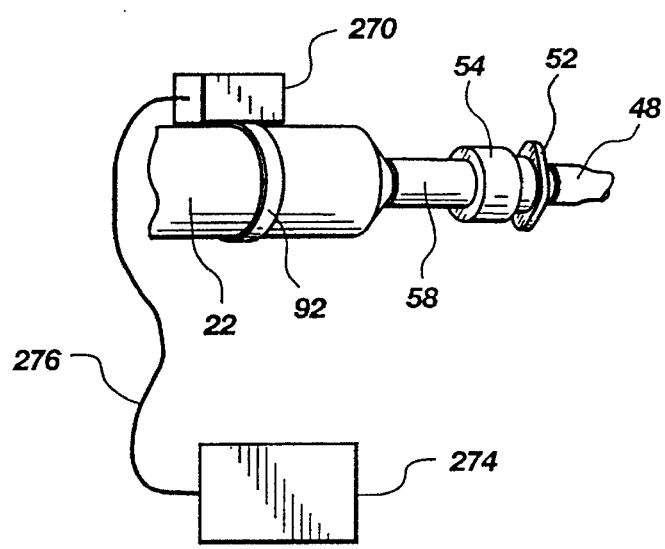
FIG. 12 shows a perspective view of an esophageal intubation detector having a transducer that provides a signal to a communication device.

Referring to FIG. 12, the indicator could be a transducer 270 connected to a communication device 274 through a wire 276. Transducer 270 could be pressure sensitive or air speed sensitive. Communication device 274 could be a loud speaker and/or a visual display. The visual display could include a liquid crystal display (LCD) or light emitting diodes (LEDs). The LCD could display words describing the condition detected. Transducer 270 could include a transmitter, and communication device 274 could include a receiver such that wire 276 is not required. Transducer 270 could be one of the indicators shown in FIG. 11. A sound detecting transducer could be placed over an audible indicator and connected to an amplifier and speaker to provide increased sound. Communication device 274 could provide positive information only that endotracheal tube 16 is in the esophagus, with the absence of the information indicating the contrary. Alternatively, communication device 274 could provide positive information that endotracheal tube 16 is either in the esophagus or the trachea.

Transducer 270 could be vented or non-vented. Under one embodiment, if transducer 270 is non-vented, the pressure sensed by it would suddenly decrease when plunger seal 78 passes orifice 28 and remain in the decreased state as long as plunger 66 is held in place. Under another embodiment, if transducer 270 is vented, the pressure sensed by it initially would be atmospheric pressure, then suddenly decrease when plunger seal 78 passes orifice 28, and then rapidly return to atmospheric pressure.

Figure 13:
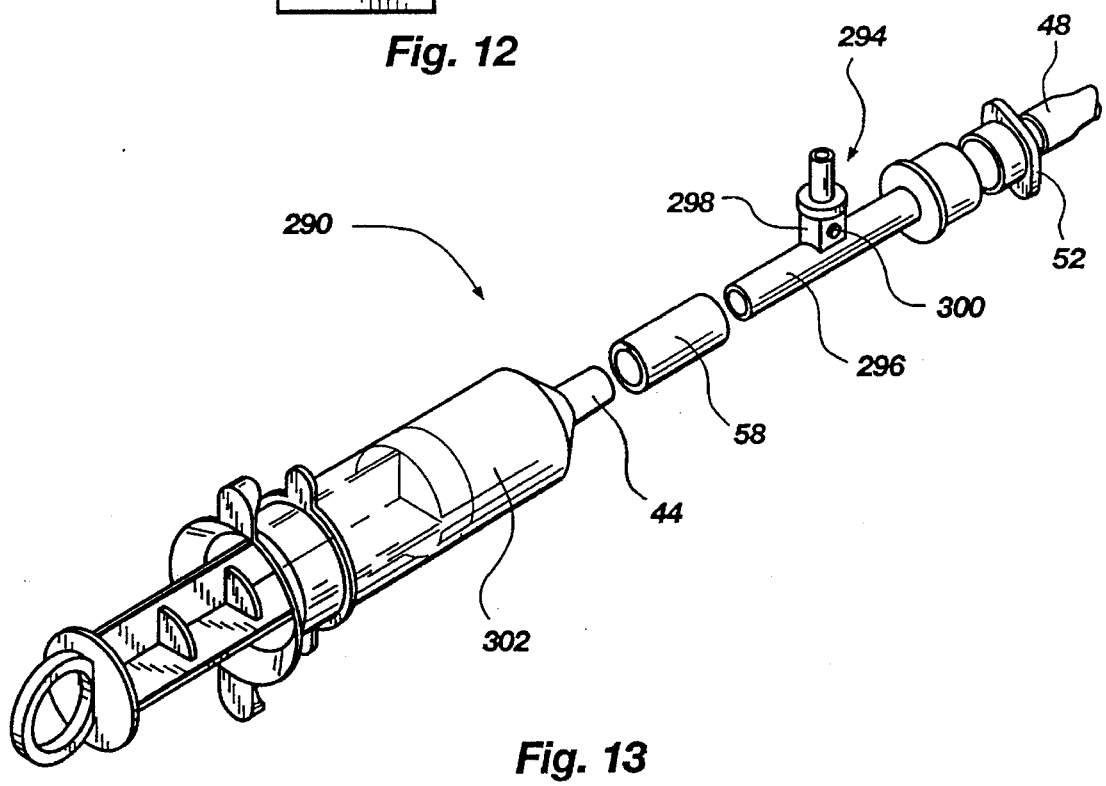
FIG. 13 is an exploded view of an alternative embodiment of an esophageal intubation detector including an indicator and connected to an endotracheal tube.
Figure 15:
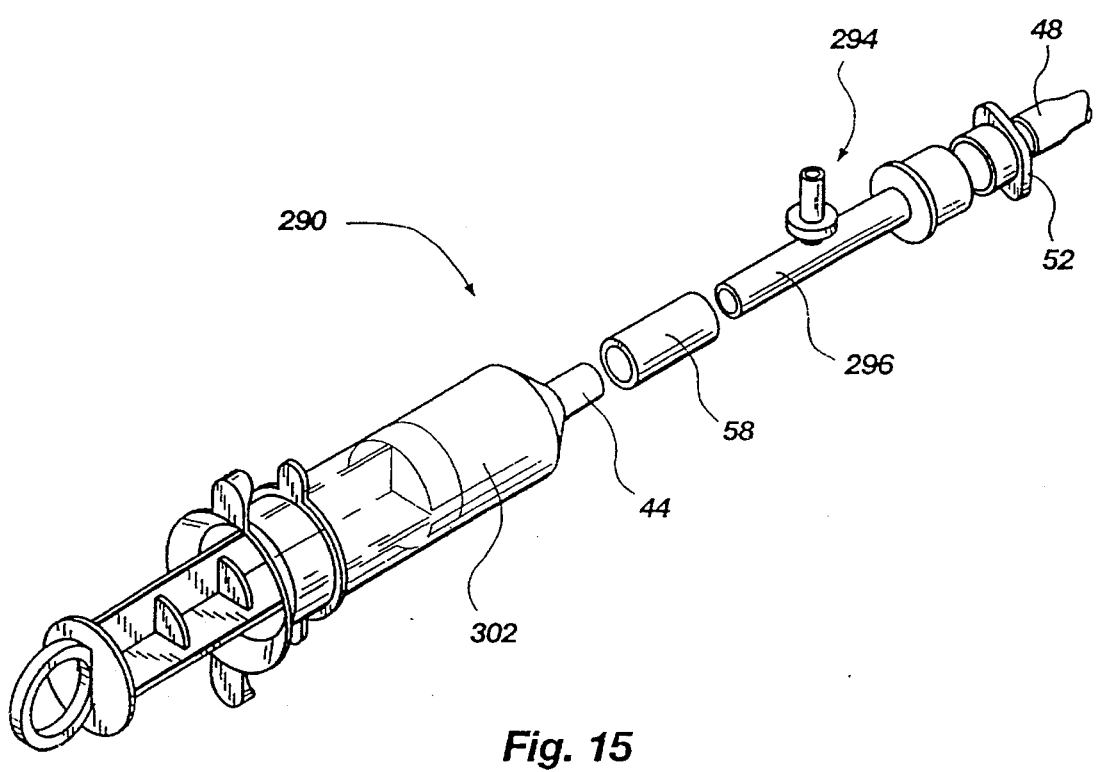
FIG. 15 shows the esophageal intubation detector of FIG. 13 without the switch housing and control switch.

FIG. 13 shows esophageal intubation detector 290, which is an alternative arrangement of esophageal intubation detector 14. An indicator 294 (which may be the same as audible indicator 36) is positioned on a switch housing 298 having a control switch 300 adapter connection tube 296. Syringe 302 does not include an orifice similar to orifice 28. After the system pressure is significantly negative due to pulling back the plunger, the clinician presses switch 300 allowing air to flow through indicator 294. Alternatively, as shown in FIG. 15, esophageal intubation detector 290 would not include switch housing 298 and control switch 300. In that case, there would not be such a large negative pressure, but there may still be enough air flow, particularly with a sensitive indicator.

Figure 14:
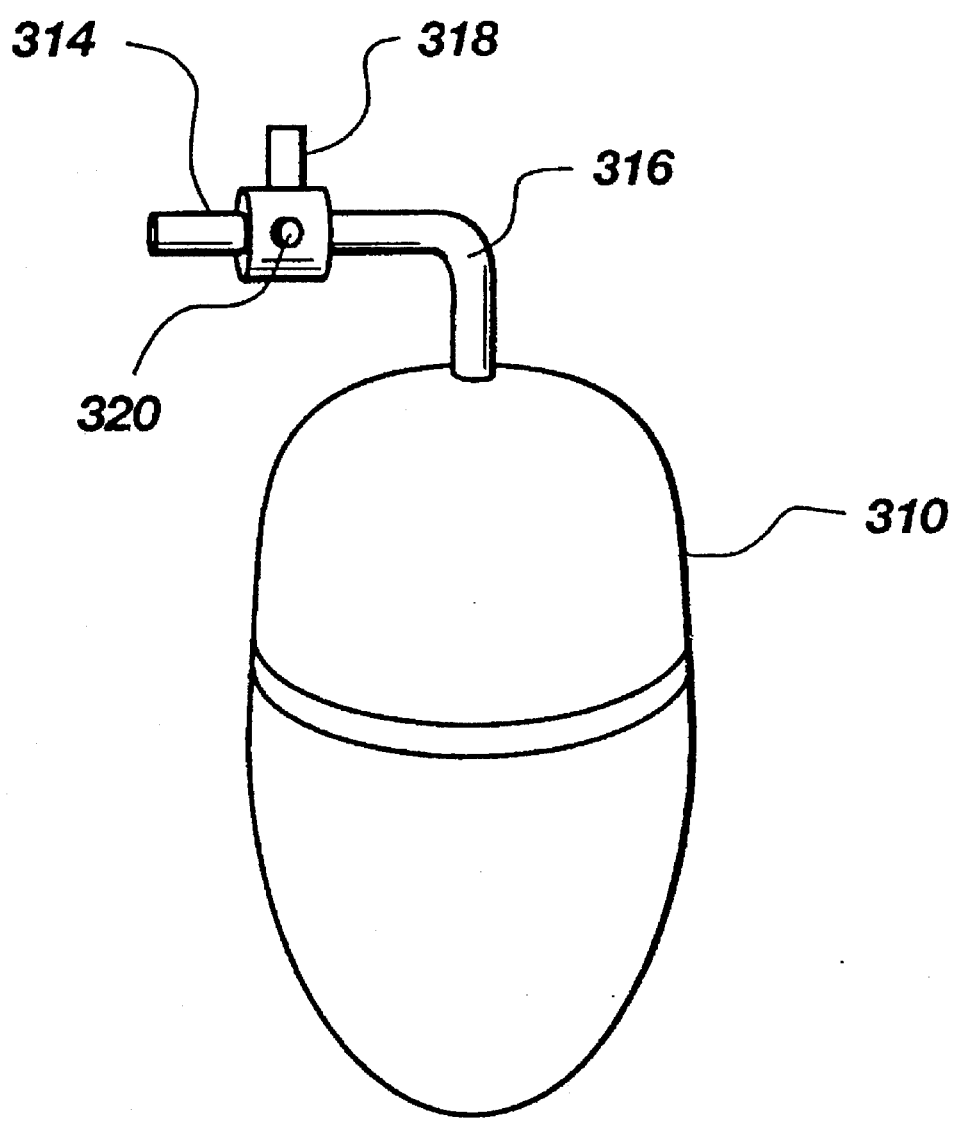
FIG. 14 shows a perspective view of an esophageal intubation detector including an evacuator bulb rather than a syringe to provide negative pressure.

Although the esophageal intubation detector preferably comprises a syringe, it may have other sources of pressure changes such as a mechanized pump or evacuator bulb. Referring to FIG. 14, a clinician may use evacuator bulb 310 to change the pressure in an endotracheal tube connected to tube 314. A tube 316 may be separated from a tube 314 by an adaptor which may include an indicator 318 and a switch 320.

As presently contemplated, orifice 28 may be approximately 0.10" (0.00254 meters) in diameter and punched or drilled in the side of the syringe barrel. Adaption piece 54 may have a 15 mm inside diameter. Endotracheal tube 16 may be of the type marketed by the Mallinckrodt company of Glens Falls, N.Y., under the catalog number 86353. A preferred syringe 20 is relatively short, has a relatively large handle, and has a volume of at least 60 cc. However, other syringes or sources of negative pressure also would be acceptable.

Various other adapters or adaption systems may be used rather than the illustrated adapter 40. For example, the adaptor may comprise a single piece or several pieces. Connector tubing 58 may be PVC tubing or shrink wrap tubing, which may be less expensive than PVC. Syringe barrel 22 and adapter 40 may be one molded component.

Although esophageal intubation detector 14 and endotracheal tube 16 are typically not connected until after initial intubation, they may be connected before initial intubation.

In the case where in the indicator is an audible indicator, an amplifier could be used to produce sufficient sound.

As used herein, the statement that the endotracheal tube is in the esophagus or the trachea means that a portion of, not all of, the endotracheal tube is in the esophagus or the trachea. Also, if holes 102A and 102B are occluded, tip 98 is said to be occluded. Further, the statement that syringe 20 is connected to endotracheal tube 16 does not require that they be directly connected. Rather, they may be indirectly connected by means of an adapter, such as adapter 40.

The present invention may be embodied in specific forms other than those of the preceding description, which are to be considered only as illustrative and not restrictive. Accordingly, the scope of the invention is indicated by the following claims, including equivalents thereof, rather than by the specific embodiments described in the preceding description.

What is claimed is:

1. An esophageal intubation detection system for use in determining whether a tip of an endotracheal tube is in a patient's esophagus or in the patient's trachea, the system comprising:

the endotracheal tube including the tube tip;

volume changing means having a cavity, for changing the volume of cavity, the cavity being connected to the endotracheal tube; and an indicator that is activated in response to a significant pressure differential across the indicator and that thereby provides an indication regarding the position of the tube tip, the indicator being pneumatically connected to the endotracheal tube and the volume changing means, whereby, if the tube tip is in the esophagus, the tube tip becomes occluded musing the significant pressure differential across the indicator as the volume of the cavity changes activating the indicator, and if the tube tip is in the trachea, the tube tip is not occluded and there is no significant pressure differential as the volume of the cavity changes.

2. The system of claim 1 in which the volume changing means is a syringe.

3. The system of claim 1 in which the endotracheal tube is connected to the volume changing means through an adapter and the indicator is directly connected to the adapter.

4. The system of claim 1 in which the endotracheal tube is connected to the volume changing means through an adapter and the indicator is positioned adjacent the adapter.

5. The system of claim 1 in which the cavity is selectively pneumatically connected to the indicator.

6. The system of claim 1 in which the indicator makes an audible sound when activated.

7. The system of claim 6 further comprising an extension tube and an ear piece, and wherein the extension tube is connected between the indicator and the ear piece.

8. The system of claim 6 further comprising a transducer proximate the indicator and amplifier that receives signals from the transducer and that amplifies the audible sound in response to the signals from the transducer.

9. The system of claim 1 in which the indicator includes a movable element that changes position when the indicator is activated, thereby providing a visual indication that the endotracheal tube is in the patient's esophagus.

10. The system of claim 9 in which the moveable element glows in the dark.

11. The system of claim 1 further comprising a communication device and in which the indicator is a transducer that provides a signal to the communication device.

12. The system of claim 11 in which the communication device has a display that displays words indicating whether intubation was proper.

13. The system of claim 11 in which the transducer includes a transmitter and the communication device includes a receiver.

14. The system of claim 1 in which the indicator is a first indicator and the system further comprises a connector tube and a second indicator, and the first and second indicators are connected by the connector tube.

15. An esophageal intubation detection system for use in determining whether a tip of an endotracheal tube is in a patient's esophagus or in the patient's trachea, the system comprising:

the endotracheal tube including the tube tip;

a syringe having a barrel with first and second orifices and a plunger with a plunger seal that fits into the barrel, the syringe being connected to the endotracheal tube through the first orifice; and an indicator that is positioned over the second orifice and that is activated in response to a significant pressure differential across the indicator, whereby if the endotracheal tube is placed in the esophagus, the tube tip is occluded and air pressure in the barrel decreases as the plunger is pulled until the plunger seal passes the second orifice at which time the significant pressure differential is created causing activation of the indicator, indicating that the endotracheal tube is in the esophagus; and if the endotracheal tube is placed in the trachea, the tube tip is not occluded and the air pressure in the barrel remains relatively constant so that the significant pressure differential is not created when the plunger seal passes the second orifice and the indicator is not activated, indicating the endotracheal tube is in the trachea.

16. The system of claim 15 in which the indicator makes an audible sound when activated.

17. The system of claim 15 in which the indicator includes a movable element that changes position when the indicator is activated, thereby providing a visual indication that the endotracheal tube is in the patient's esophagus.

18. The system of claim 15 in which the syringe is connected to the endotracheal tube through the first orifice and an adapter.

19. The system of claim 15 in which the indicator is activated in response to flow of air through the indicator caused by the significant pressure differential.

20. The system of claim 1 in which the indicator is non-vented.

21. An esophageal intubation detection system for use in determining whether a tip of an endotracheal tube is in a patient's esophagus or in the patient's trachea, the system comprising:

an adapter having an orifice;

the endotracheal tube including the tube tip, the endotracheal tube being connected to the adapter;

a syringe having a plunger and a barrel with a barrel tip, the syringe being connected to the adapter; and an indicator positioned over the orifice of the adapter, the indicator being activated in response to a significant pressure differential across the indicator;

whereby, if the tube tip is in the esophagus, the tube tip becomes occluded as the syringe plunger is pulled away from the barrel tip causing the pressure in the adapter to decrease until the significant pressure differential exists across the indicator activating the indicator which indicates that the tube tip is in the esophagus; and if the tube tip is in the trachea, the tub tip does not become occluded as the syringe plunger is pulled away from the barrel tip, the pressure in the adapter does not significantly decrease, and the indicator is not activated.

22. An esophageal intubation detection system for use in determining whether a tip of an endotracheal tube is in a patient's esophagus or in the patient's trachea, the system comprising:

the endotracheal robe including the tube tip;

a collapsible self inflating cavity;

an adapter including an orifice, the adapter being connected to the endotracheal tube and the collapsible self inflating cavity; and an indicator that is positioned over the orifice and that is activated in response to a signifier pressure differential across the indicator, whereby if the endotracheal tube is placed in the esophagus, the tube tip is occluded and air pressure in the adapter decreases as the collapsible self inflating cavity inflates causing the significant pressure differential and activation of the indicator, indicating that the endotracheal tube is in the esophagus; and if the endotracheal tube is placed in the trachea, the robe tip is not occluded and the air pressure in the adapter remains relatively constant as the self inflating cavity inflates so that the significant pressure differential is not created and the indicator is not activated, indicating the endotracheal tube is in the trachea.

* * * * *

UNITED STATES PATENT AND TRADEMARK OFFICE
CERTIFICATE OF CORRECTION

PATENT NO. : 5,487,731

DATED : January 30, 1996

INVENTOR(S) : Denton

It is certified that error appears in the above-indentified patent and that said Letters Patent is hereby corrected as shown below:

In Column 6, line 66, after "300" insert --that in turn is positioned on an--;

In Column 7, line 61, after "means" insert --,-- (comma);

In Column 7, line 62, after "of" insert --the--;

In Column 8, line 4, change "musing" to --causing--;

In Column 10, line 4, change "tub" to --tube--;

In Column 10, line 13, change "robe" to --tube--;

In Column 10, line 20, change "signifier" to --significant--; and

In Column 10, line 28, change "robe" to --tube--.

Signed and Sealed this

Twentieth Day of August, 1996

Attest:

BRUCE LEHMAN

*Attesting Officer*   *Commissioner of Patents and Trademarks*